(12) United States Patent
Izvoztchikov et al.

(10) Patent No.: US 6,209,437 B1
(45) Date of Patent: *Apr. 3, 2001

(54) MICROTOME

(75) Inventors: Ilia Izvoztchikov, Petersburg (RU); Hans Heid, Bammental (DE)

(73) Assignee: Micron Laborgerate GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,740
(22) PCT Filed: Aug. 14, 1995
(86) PCT No.: PCT/EP95/03219
§ 371 Date: May 6, 1997
§ 102(e) Date: May 6, 1997
(87) PCT Pub. No.: WO96/05495
PCT Pub. Date: Feb. 22, 1996

(30) Foreign Application Priority Data

Aug. 15, 1994 (RU) .................................................. 94030222

(51) Int. Cl.[7] ................................. B26D 7/06; G01N 1/06
(52) U.S. Cl. ............................................. 83/707; 83/915.5
(58) Field of Search ..................................... 83/915.5, 707

(56) References Cited

U.S. PATENT DOCUMENTS

| 2,155,523 | * | 4/1939 | Bausch et al. | ....................... 83/915.5 |
| 2,743,404 | * | 4/1956 | Storey, Jr. et al. | ..................... 83/707 |
| 3,399,630 | * | 9/1968 | Wilson | ................................... 83/707 |
| 3,828,641 | * | 8/1974 | Sitte | ..................................... 83/915.5 |
| 4,126,069 | * | 11/1978 | Shimonaka | .......................... 83/915.5 |
| 4,539,877 | * | 9/1985 | Stevenson | .............................. 83/707 |
| 4,598,621 | * | 7/1986 | Weinhold | ............................. 83/915.5 |
| 5,461,953 | * | 10/1995 | McCormick | ......................... 83/915.5 |
| 5,461,957 | * | 10/1995 | Koch et al. | ............................. 83/707 |
| 5,535,654 | * | 7/1996 | Niesporek et al. | ..................... 83/707 |

FOREIGN PATENT DOCUMENTS

| 3301921 | | 7/1984 | (DE) . |
| 3539138 | | 11/1985 | (DE) . |
| 0416354 | | 3/1991 | (EP) . |
| 330591 | * | 7/1903 | (FR) | ................................... 83/915.5 |
| 783626 | | of 0000 | (SU) . |

* cited by examiner

*Primary Examiner*—M. Rachuba
*Assistant Examiner*—Sean Pryor

(57) ABSTRACT

The microtome has a sample carrier movable along a first linear guide and a hand drive movable along a substantially linear path of motion that is substantially perpendicular to the direction of motion of the sample carrier. A deflecting device is provided to deflect the motion of the hand drive into a motion in the direction of the linear guide of the sample carrier. By deflection of the paths of motion between the hand drive and the sample holder, the motion of the hand drive can take place substantially horizontally forward and backward and convert the motion of the hand drive into a motion of the sample carrier which is substantially perpendicular to the motion of the hand drive. The cutting motion takes place in a substantially vertical direction, so that the sections can be removed or washed away from the inclined back surface of the cutting knife or knife carrier.

24 Claims, 4 Drawing Sheets

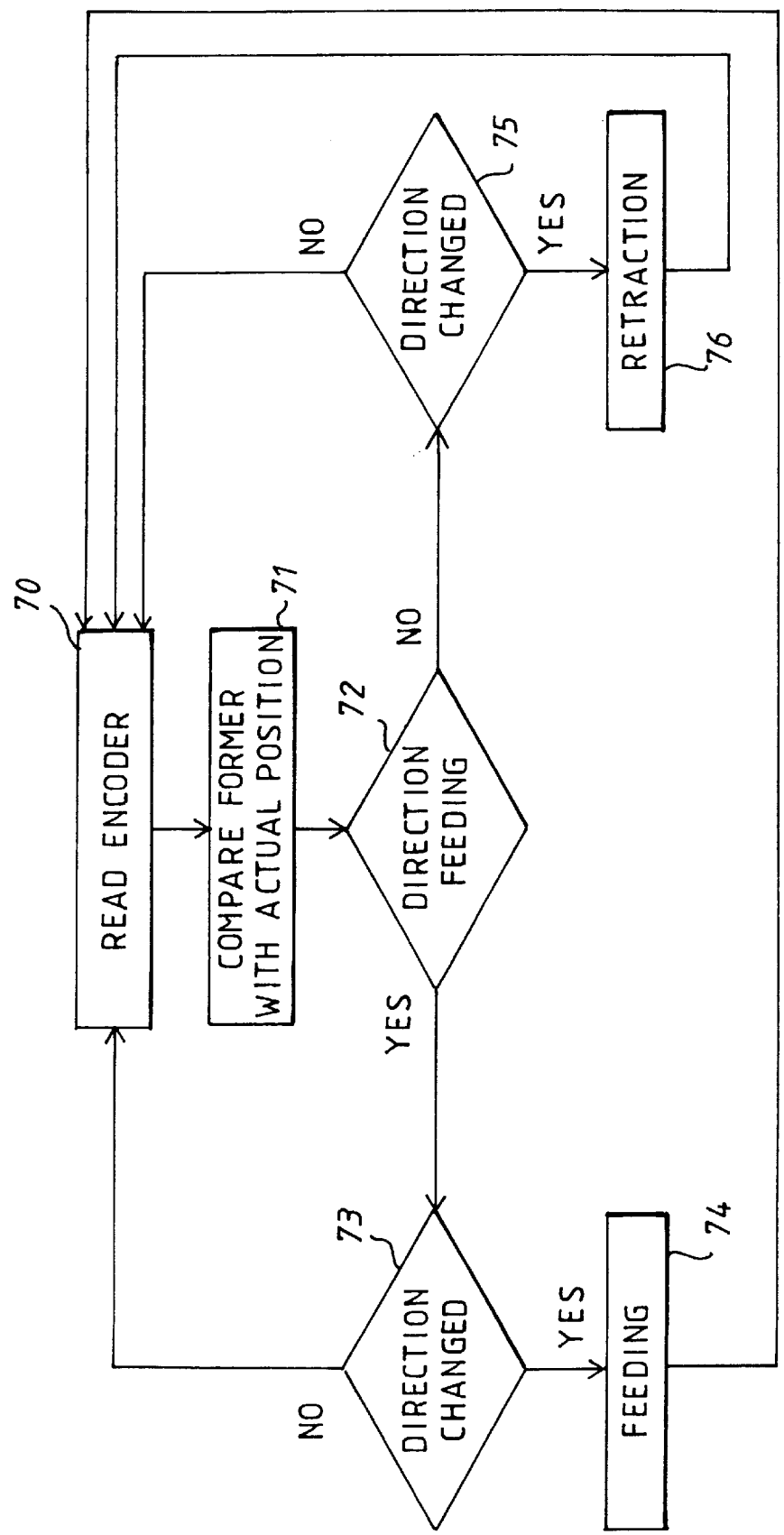

MICROTOME

BACKGROUND OF THE INVENTION

1. Field of the Invention

The invention relates to a microtome for the production of histological sections, particularly of plant and animal tissues, which are intended for microscopic inspection.

2. Discussion of Prior Art

So-called slide microtomes are known from the Soviet Inventor's Certificate SU-783626 or from the Applicant's EP-A1 0 416 354, and have a baseplate with an object carrier and in addition substantially horizontal guides. A knife holder is movably received in the horizontal guides and is provided with a handle. The knife holder moves back and forth, linearly and horizontally, and its motion is coupled with a feed drive of the sample carrier.

Slide microtomes are distinguished by their simple construction and the consequent low price. Moreover they are distinguished, as long as the user follows a sufficient routine, by operation which is not tedious. On the other hand, it is a disadvantage that the removal of the microtome sections is quite complicated. This disadvantage clearly becomes manifest in the latest slide microtomes, which have an electrical drive of the sample feed, such as that offered by the Applicant under the designation "OHM 440". Indeed, because of the electrical sample feed, the knife holder no longer needs to be moved over the whole length of the guideway in order to cause the sample feed. Instead, it is sufficient to move the knife or the knife holder over a path length which roughly corresponds to the thickness of the sample along the direction of cutting, since the electronics of the sample feed detects the reversal of motion of the knife holder. Thus with small samples, a substantially higher cutting frequency is possible. However, it has been found that the time required for removal of sections limits the cutting frequency.

Moreover, so-called rotary microtomes are known, which are described, for example, in DE-P 33 01 921 or in DE-C1 35 39 138. Such a rotary microtome usually has a baseplate on which a slide with a cutting knife, movable parallel to the baseplate, is received. The slide with the sample carrier is received in a further guide, which is directed substantially perpendicular to the baseplate and consequently permits a motion of the sample carrier perpendicular to the baseplate. The drive of the cutting motion, which runs perpendicular to the baseplate, of the sample carrier takes place by means of a hand crank in the form of a disc with a horizontal axis of rotation.

As regards removal of sections, such rotary microtomes are considerably more user-friendly than slide microtomes, since the sections which are produced are produced in the forward region of the microtome, lie on the back face, inclined forward and downward, of the microtome knife or knife holder, and can be floated off there, for example by the use of a water bath. However, such rotary microtomes have the disadvantage that the rotary motion of the handle is quite tiring. The number of sections produced during the course of a working day is thus lower for rotary microtomes than for slide microtomes.

It would be conceivable to provide a motor to drive the cutting motion, in order to eliminate this disadvantage. However, the motors which would be required for this would nearly double the price of the microtome.

SUMMARY OF THE INVENTION

The invention therefore has as its object to provide a microtome with a hand drive for the cutting motion, which microtome is not very tiring to operate, and at the same time enables the sections which are produced to be easily removed.

This object is attained by a microtome having a first linear guide, a sample carrier movable in a guide direction along the first linear guide, a hand drive movable along a substantially linear path of motion substantially perpendicular to the guide direction of the first linear guide and a deflecting device for deflecting motion of the hand drive into motion in the guide direction of the first linear guide.

The microtome according to the invention has a sample carrier which is movable along a first linear guide. Moreover, the microtome has a hand drive which is movable along a substantially linear path of motion, wherein the path of motion of the hand drive is substantially perpendicular to the direction of motion of the sample carrier. Furthermore, means are provided to deflect the motion of the hand drive into a motion in the direction of the linear guide of the sample carrier.

By the deflection of the paths of motion between the hand drive and the sample holder, the motion of the hand drive can take place substantially horizontally forward and backward of the microtome (push and pull motion by the operator), which is considered to be particularly favorable from the ergonomic viewpoint, and can be converted into a motion of the sample carrier, substantially perpendicular to the motion of the hand drive. The cutting motion can thus take place in a substantially vertical direction, so that the sections which are produced can be removed or washed away from the inclined back surface of the cutting knife or knife carrier.

The result of the invention is a microtome which unites the respective specific advantages of both the slide microtome and the rotary microtome, without having the specific disadvantages of each of these types of construction.

The means for deflection of the motion can be constructed, in a simple embodiment example, as a belt drive which is guided over several deflecting rollers. Of course, a belt drive makes possible only an integer transmission ratio between the motion of the hand drive and that of the sample carrier. A counterweight is to be provided, for weight equalization, on the driving belt of the belt drive, having a mass which corresponds to the transmission ratio and to the mass of the sample carrier including its guide slide, chosen such that the two masses equalize each other in each position of the sample carrier.

Alternatively to this, the means for deflection of the direction of motion can be constructed as a plate in the form of a circular segment, or as a lever arm. According to the ratio of the two arm lengths of the lever arm, or according to the ratio of the distances of the deflection points from the mounting point of the circular segment shaped plate, different, and even non-integral, transmission ratios can be set in this embodiment between the motion of the hand drive and that of the sample carrier. The use of a hydraulic system for the deflection of the motions likewise makes possible optional, even non-integral, transmission ratios.

In an advantageous embodiment example of the invention, a device is provided for the detection of a reversal of motion of the sample carrier. By the detection of the reversal of motion, control of the forward feed of the sample can take place independently of the path lengths of the cutting motion. The path length of the sample carrier can be chosen by the user himself, corresponding to the thickness of the sample which is about to be cut, and does not need to pass, in order to release the feeding of the return stroke, along a minimum path which is determined by the construction.

The detection of the reversal of motion is particularly advantageous in connection with a motor drive for the sample feed, and with an electronic control circuit which controls the motor in the case that a reversal of motion is detected.

In a further advantageous embodiment example, a hand drive is provided, or a hand drive can be installed, on two mutually opposite sides of the microtome. The ergonomic advantages of the microtome according to the invention can thus be fully realized for both left-handed and right-handed persons.

Furthermore, in the microtome according to the invention, the knife carrier of the microtome is to be movable, for the sample feed, along linear guideways perpendicular to the cutting motion of the sample holder. The masses to be accelerated during the cutting motion can thus be kept to a minimum, since the mechanism for the sample feed does not count as part of the masses to be accelerated. The invention are described in further detail hereinbelow with reference to the embodiment examples shown in the accompanying Figures.

BRIEF DESCRIPTION OF THE DRAWINGS

Perferred embodiments of the present invention will now be described, taken together with the drawings, in which:

FIG. 3b shows a front view of the microtome in FIG. 3a;

FIG. 5 shows a block circuit diagram relating to the control of the sample feed and return stroke.

DETAILED DESCRIPTION OF THE PERFERRED EMBODIMENTS

Figure 1:
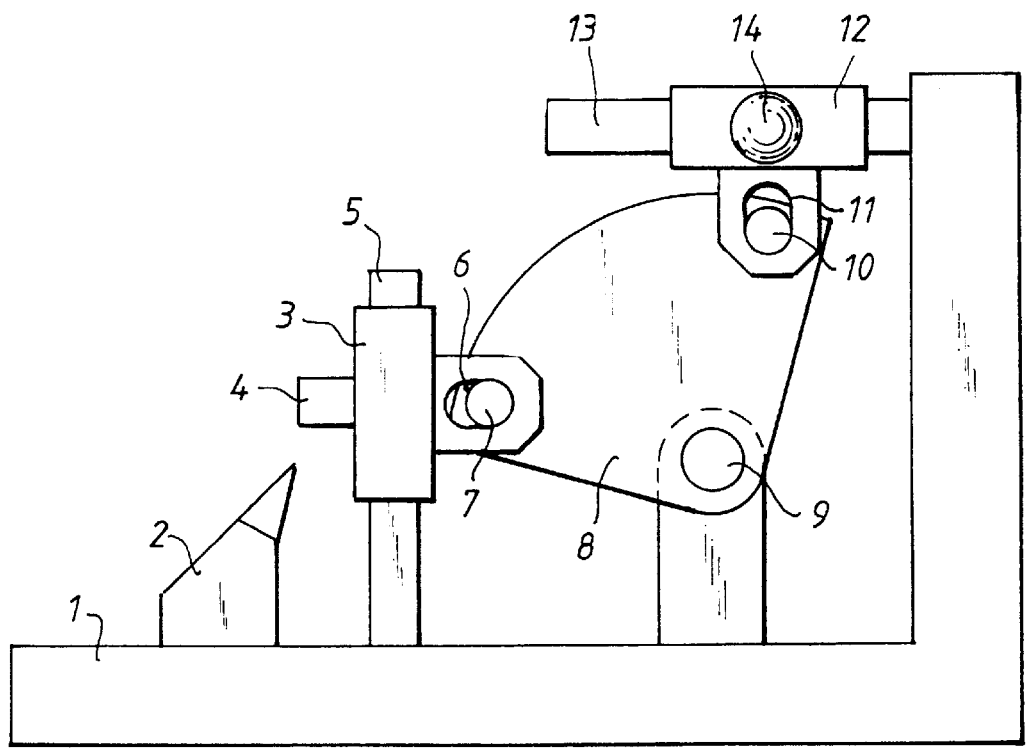
FIG. 1 is an elementary sketch of a first embodiment example of the invention with a plate in the form of a circular segment as means for deflection of the motion.

The embodiment according to FIG. 1 contains a baseplate (1), on which the knife carrier (2) is received in the forward region, facing the user, and is movable back and forth horizontally, that is, in the direction of the baseplate (1). The sample carrier (3), with a sample (4), is received, vertically movable, on a guide (5) which is oriented perpendicularly to the baseplate (1). The guided slide of the sample carrier (3) has a groove (6) in which there engages a pin (7) of a plate (8) of circular segment shape. The circular segment plate (8) is mounted for rotation about a rotation axis (9). The plate (8) has a second pin (10), spaced apart from the first pin (7), and engaging in the groove (11) of a horizontally guided slide (12). A horizontal guideway (13) is connected to the baseplate (1) of the microtome in order to guide the slide (12). A handle (14) for the manual operation of the cutting motion is provided on the slide (12).

The circular segment plate (8) with the two pins (7) and (10) forms a unit for the transmission and deflection of the horizontal motion of the handle (14) into the substantially vertical direction of motion of the sample carrier (3). The slide (12), the guide (13), and the handle (14) form a hand drive device.

For the operation of the microtome of FIG. 1, the user displaces the slide (12) along the horizontal guides (13) towards himself, by means of the handle (14). Upon this motion of the slide (12), the pin (10) engaging in the groove (11) rotates the plate (8) counter-clockwise, and with it the attached pin (7) which engages in the groove (6) of the sample carrier (3). The sample carrier (3) is thereby moved in the direction towards the cutting knife of the microtome. As a result of this motion, the cutting of a section of the sample (4) takes place. Upon the subsequent motion of the handle (14) rearward away from the user, the sample carrier (3) is again lifted up and the feed drive (not shown in the drawing) of the knife carrier (3) executes a horizontal motion rearward through a predetermined path length, in the direction towards the sample carrier (3). Upon the subsequent motion of the handle (14) forward again, the cutting of a further section from the sample takes place.

Figure 2:
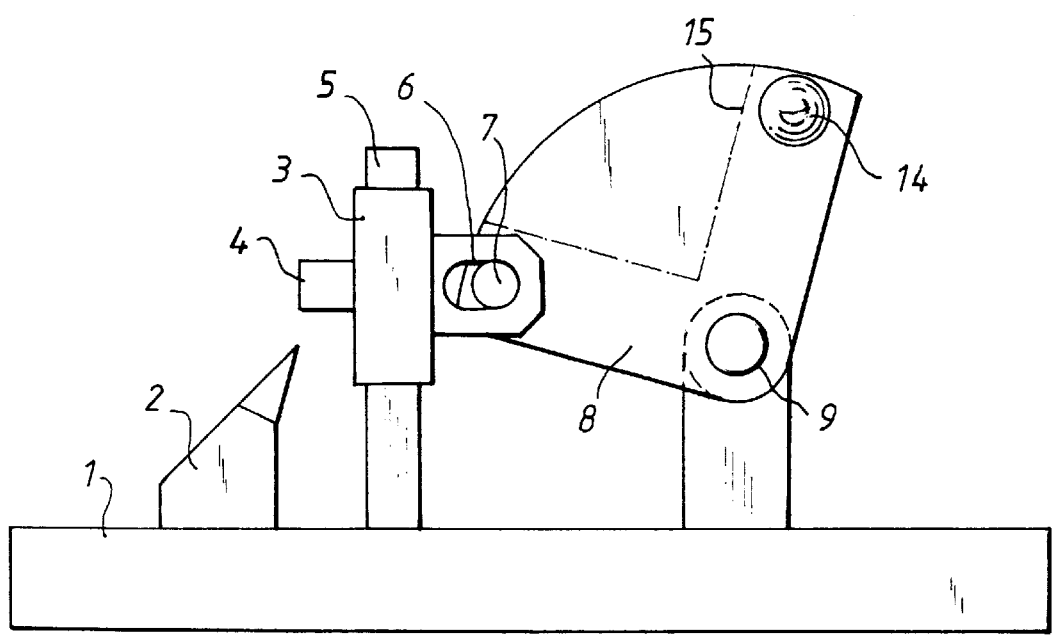
FIG. 2 is an elementary sketch of a simplified form of the embodiment according to FIG. 1.

The embodiment according to FIG. 2 is a simplified form of the embodiment according to FIG. 1. The constructional elements denoted by 1 through 9 correspond to those of FIG. 1, and are therefore not further described here. Differing from the embodiment according to FIG. 1, the handle (14) is received directly at the place on the circular segment plate (8) at which the pin (10) is provided in the mode of embodiment according to FIG. 1. In this embodiment, the circular segment (8) and its axis of rotation (9) simultaneously serve as parts of the hand drive device and of the device for the transmission and deflection of the motion from the handle to the sample carrier (3). In this embodiment, the path of motion of the handle (14) is not exactly linear, but is a section, running substantially horizontally, of a circular path. This deviation can hardly be detected by the operator, however, since the handle (14) is distanced sufficiently far from the rotation axis (9) of the circular segment (8) and consequently the radius of the circular path is greater by at least a factor of 2 than the path length along the circular path.

Instead of a plate (8) of circular segment shape, the deflection of the direction of motion from the hand drive (14) to the sample holder (3) can also be realized by a pivotably mounted lever arm. Such a lever arm is derived in a simple manner from the circular segment shaped plate (8) if this is cut along the lines (15), shown dashed in FIG. 2, parallel to the connection axes between the handle (14) and the rotation axis, and between the pin (7) and the rotation axis (9).

The increase or reduction transmission ratio of the motions of the sample carrier and of the hand drive can be optionally realized according to the ratio of the two effective lever lengths.

Figure 3B:
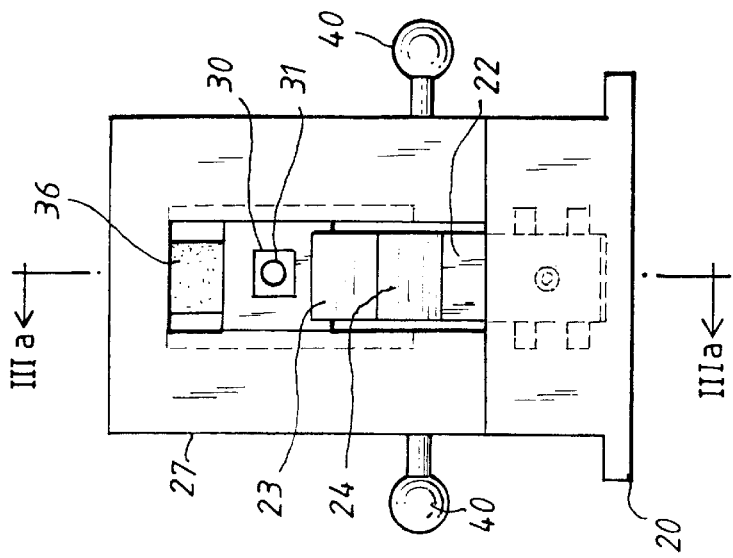
Figure 3A:
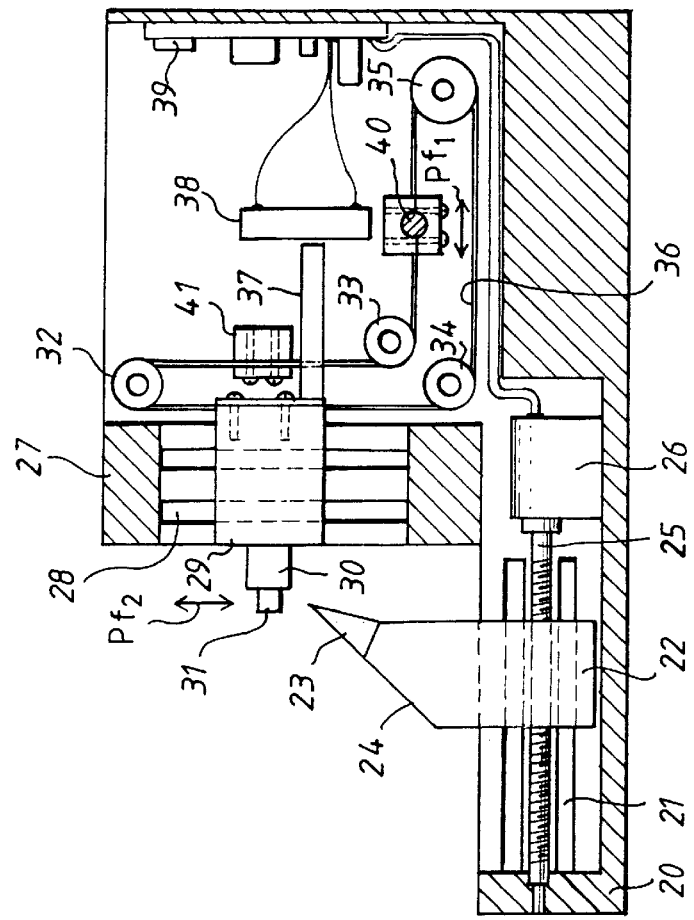
FIG. 3a shows, in section, a microtome with a belt drive and a 1:1 transmission ratio between the motion of the hand drive and the motion of the sample carrier.

In the embodiment example according to FIG. 3a, the baseplate of the microtome is denoted by (20). The guideways (21), extending along the baseplate (20), are provided in the baseplate (20) for the feed motion of the knife carrier (22). The cutting knife (23) is received on the knife carrier (22). A stepping motor (26) is provided for driving the feed motion, and has a threaded spindle (25) which runs parallel to the guideways (21) and which is screwed into a corresponding internal thread in the knife carrier (22).

A portal frame (27) which stands substantially perpendicularly of the baseplate (20) and which has guideways (28) is fixedly arranged on the baseplate (20). The sample carrier (30) with the sample (31) to be cut is received in the forward region of the sample carrier slide (29).

On the side remote from the sample carrier (30) is a driving belt (36), for example, a wide steel band or a V-belt, which is guided by a total of four deflection rollers (32–35), and which is screwed to the sample carrier slide (29). Two deflecting rollers (32, 34) of the four deflecting rollers (32–35) insure that the driving belt (36) is guided in the forward region parallel to the guideways (28) in the portal frame (27). The other two deflecting rollers (33, 35) serve to insure that the driving belt (36) in the region of the handle (40) is guided perpendicularly of the guideways (28) in the portal frame (27). Thus when the handle (40) moves horizontally in the direction of the double arrow (Pf1), a vertical motion results of the sample carrier slide (29) in the direction of the double arrow (Pf2).

The four deflecting rollers (32–35) also insure that the cutting motion takes place when the handle (40) is pulled towards the user. Moreover, it is insured that the handle (40) is arranged in the lower part of the microtome, in the neighborhood of the baseplate (20). Both of these features are particularly favorable from the ergonomic viewpoint.

The use of four deflecting rollers furthermore insures that the driving belt (36) runs about vertically between two further deflecting rollers (32, 33), the direction of motion of the belt (36) in this region being the reverse of the direction of motion at the sample carrier slide (29). A balance weight (48) is provided on the driving belt (36) between these two deflecting rollers (32, 33); its mass corresponds to that of the sample carrier slide (29) with the sample carrier (30). Due to this weight equalization, the sample carrier slide remains stationary at any position of the guideway (28) where it is placed, so that only the required accelerating forces, but no additional weight forces, have to be applied at any place when the motion is reversed by means of the handle (40).

The drive pin (37) of a slide potentiometer (38) is also provided on the side of the sample carrier slide (29) remote from the sample carrier (30). When the sample carrier slide (29) moves, the resistance of the potentiometer (38) changes correspondingly. The voltage drop at the potentiometer (38), or more precisely the change of this voltage drop, serves for the detection of the reversal of motion of the sample carrier slide (29) and for the corresponding control of the motor (26) for the feed motion. The required evaluation electronics (not shown) is provided on a board (39) within the microtome, and the individual steps which take place in it are described in detail hereinbelow with reference to FIG. 5.

FIG. 3b shows the front view of the microtome of FIG. 3a. As is known, a respective handle (40) is provided on each of two opposite sides of the microtome, to drive the cutting motion of the sample carrier slide (29). The microtome thus has the same ergonomic advantages for right-handed and left-handed people. It is of course also possible to provide, instead of two handles (40), only a single handle (40) which can be selectively fitted by the user to one of the two opposite sides of the microtome.

Figure 3C:
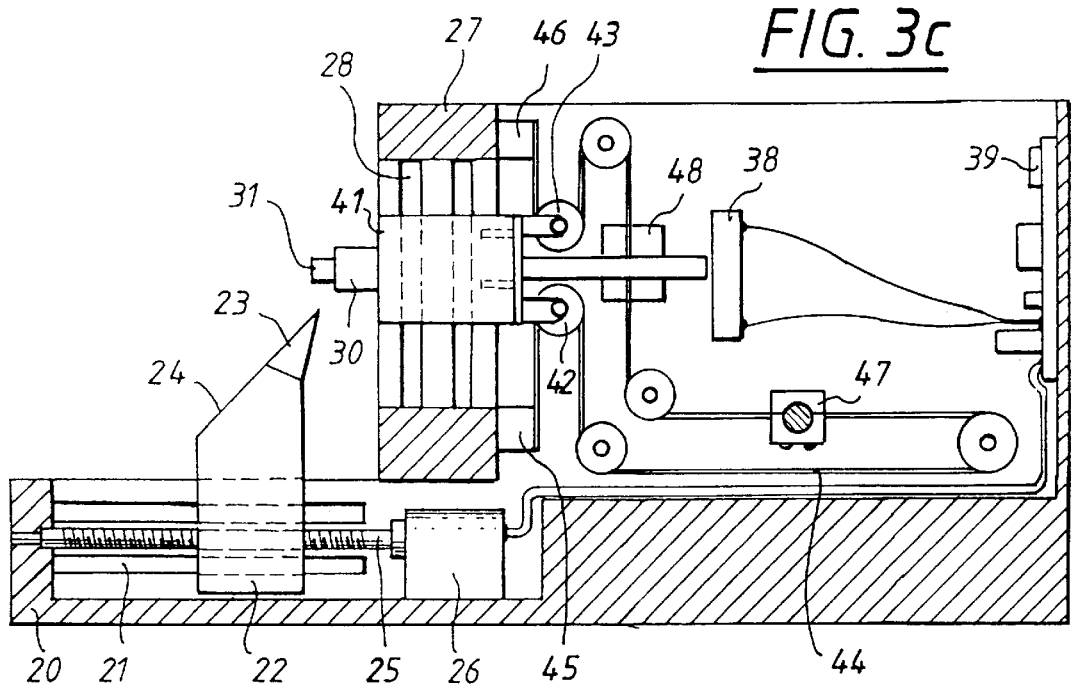
FIG. 3c shows a sectional view of a microtome with a belt drive for a 2:1 transmission ratio between the motion of the hand drive and the motion of the sample carrier.

In the microtome of FIGS. 3a and 3b, the transmission ratio between the motion of the hand drive (40) and the sample carrier slide (29) is 1:1. In this case, the driving belt (36) is constructed as a circulating endless belt. In contrast to this, the sample carrier slide (41) itself, in the embodiment example according to FIG. 3c, has two rotatable deflecting rollers (42, 43), over which the driving belt (44) is trained. The driving belt is constructed as a belt having two ends in this embodiment example and runs with its ends parallel to the guideways of the sample carrier slide (41), and is fastened at its ends, by means of spacers (45, 46) to the portal frame (27), which has the guideways for the sample carrier slide (41) of the microtome. In this embodiment, the motion of the hand drive (47) is stepped down in a ratio of 2:1 to the motion of the sample carrier slide (41); this means that the required stroke of the hand drive (47) is twice as large as the stroke of the sample carrier slide (41). The mass of the balance weight (48) needs only to amount to half the mass of the sample carrier slide (41) with the sample holder (30) received on it, giving an overall reduction of the masses to be accelerated.

Moreover, the forces required for the acceleration of the sample carrier slide (41) are only half as large, due to the 2:1 reduction ratio, as those in the case of a 1:1 transmission ratio, so that the total accelerating forces which have to be applied amount to less than half of those in the embodiment example according to FIG. 3a. The detection of the reversal of motion of the sample carrier slide (41) and the corresponding drive of the motor for the advance of the microtome knife takes place in the same manner as in the embodiment example according to FIG. 3a, and is therefore not described again here.

Figure 4:
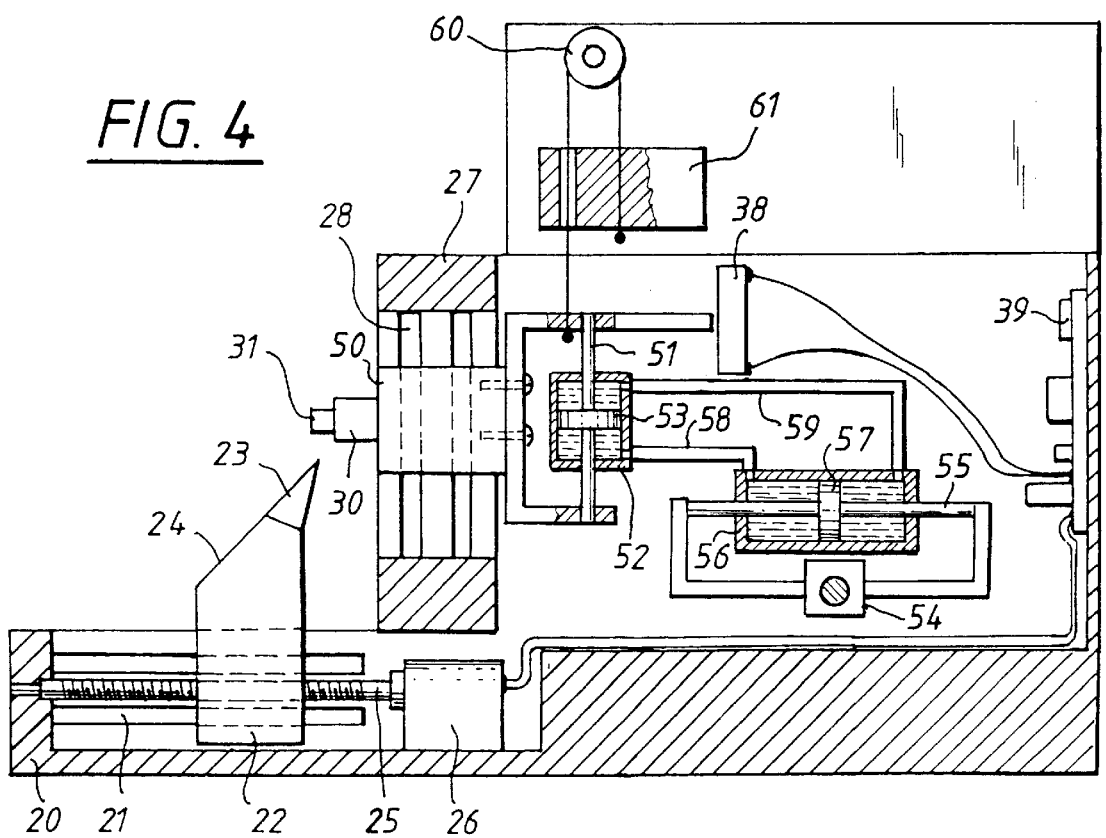
FIG. 4 shows a sectional view of a microtome with a hydraulic transmission of the motion of the hand drive to the motion of the sample carrier.

In the embodiment example according to FIG. 4, a hand-operated hydraulic system is provided for driving the cutting motion of the sample carrier slide (50). For this purpose, the hand drive knob (54) is connected by a rod (55) to a displacement piston (57) in a first hydraulic cylinder (56). This hydraulic cylinder (56) is connected by means of two hydraulic ducts (58, 59) to a second hydraulic cylinder (52), the displacement piston (53) of which is rigidly connected via a rod (51) to the sample carrier slide (50). When the drive knob (54) is moved towards the front side of the microtome, the displacement piston (57) pushes the hydraulic oil in the first cylinder (56) through the duct (58) into the second hydraulic cylinder (52) and pushes its displacement piston upwards, so that the sample carrier slide (50) is likewise moved upwards. Simultaneously, the displacement piston (53) pushes the excess hydraulic oil in the upper chamber of the second hydraulic cylinder (52) via the second duct (59) into the rear chamber of the first hydraulic cylinder (56). When the handle (54) is moved in the reverse direction, the corresponding reverse functional sequence takes place, so that the sample carrier slide (50) is guided downwards for the cut. The cut correspondingly takes place, in the embodiment example according to FIG. 4, during is pushing motion of the hand drive (54), in contrast to the pulling motion in the embodiment examples according to FIGS. 3a and 3c. If it is desired that, in the case of a hydraulic force transmission to the sample carrier slide, the cutting motion is effected downwards during a pulling motion, that is, a motion of the handle (54) forwards, it is only necessary to interchange the connections of the two ducts (58 and 59) to the second hydraulic cylinder (52). For weight equalization, a counterweight (61) is also provided in this embodiment example, and is attached to the sample carrier slide (50) by means of a cord which is trained over a roller (60).

In this embodiment example also, a reversal of the motion of the sample carrier slide (50) is detected by means of a slide potentiometer (38), and when a reversal is detected, the stepping motor (26) is controlled for driving the feed motion of the microtome knife.

In the embodiment examples which have been described, the sections which are produced lie on the back face (24), which is inclined downwards and forwards, of the knife carrier, in the front region of the microtome, so that the sections can be easily and conveniently removed or floated off, as in rotary microtomes.

FIG. 5 shows details of the functional steps which take place in a control processor of the electronics board (39) for the detection of the reversal of motion of the sample carrier slide. In a first step (70), the value of the position transducer, that is, the resistance of the slide potentiometer (38) set at that moment, is read out and temporarily stored. In a subsequent step (71), the instantaneous resistance is compared with the stored resistance of the previous measurement; this can take place, for example, by the formation of a difference or quotient of the actual value with the previous value. In a subsequent step (72), it is decided from the comparison value whether a cutting motion (sample carrier slide is moved downwards) or a return motion (sample carrier slide is moved upwards) is taking place. It is correspondingly decided whether the knife carrier is to next execute a feed motion or a return motion. In the case that a cutting motion is ascertained, it is decided in a subsequent function step (73), by a comparison of the direction of motion during the previous measurement, whether the direction of motion has reversed. If this question is answered in the negative, the position transducer is read afresh, and the routine is run through anew. If on the other hand a reversal of the direction of motion was detected in function step (73), the motor (26) is subsequently controlled such that the knife carrier (22) is moved in the direction towards the portal frame (27) over a path length which corresponds to the sum of a return stroke distance and a predetermined section thickness. After this, the routine returns to the first function step (70), so that the position transducer is read out anew and the routine is run through anew.

In the case that a return motion was detected in the function step (72), it is ascertained in the subsequent function step (75), by a comparison with the direction value of the previous measurement, whether a reversal of direction has taken place. If this question is answered in the negative, the routine returns to the function step (70), the position transducer is read out anew, and the routine is run through anew. If on the other hand a reversal of the direction of motion is detected in the function step (75), which means that a change from a cutting motion to the return motion had taken place between the present measurement and the previous measurement, the stepping motor (26) is then controlled in a subsequent function step (76) such that the knife carrier (22) is moved away from the portal frame (37) of the microtome through the predetermined return stroke. The routine then returns again to the function step (70), the position transducer is read out anew and the routine is run through anew.

In order to insure that a feed motion or return motion is not started every time there is a small shaking of the hand drive (40), it is also respectively tested in the function steps (73 and 75) whether at least one predetermined safe path, which has a value between 2 mm and 5 mm, was carried out in the same direction. Otherwise, it is decided by the routine in function steps (73 and 75) that no reversal of motion has taken place.

Detection of the reversal of motion for the release of the feed or of the return insures that this release also reliably takes place when the user limits the length of the cutting motion and the return motion to the minimum which is predetermined by the object to be cut. In particular, with small samples, the user can execute very short motions, based on the detection of the reversal of motion together with the linear motion of the hand drive (40), so that long idle paths of the cutting and return motion are avoided. A high cutting frequency can thus be obtained, particularly with small samples.

In the examples shown in FIGS. 3a–3c and 4, the guides of the sample carrier slide and the hand drive are exactly perpendicular to each other. Such an arrangement is provided for equipment which is to be placed on a horizontal support. However, it is also possible to construct the microtome to be placed on an inclined surface, as for example in cryostatic microtomes, the motion of the sample carrier slide being inclined at an angle of up to 30° to the vertical. In such embodiment examples, the deflection angle between the motion of the sample carrier slide and that of the hand drive are to be chosen such that the motion of the hand drive takes place in the horizontal direction in this case also.

We claim:

1. A microtome, comprising:
   a first linear guide (5, 28),
   a sample carrier slide (3, 29, 41, 50) moveable in a guide direction along said first linear guide (5, 28),
   a hand drive, said hand drive including a hand drive handle (14, 40, 47, 54) moveable along a substantially linear path of motion substantially perpendicular to said guide direction of said first linear guide (5, 28), said substantially linear path of motion of said hand drive handle (14, 40, 47, 54) having a fixed direction, and
   a deflecting device (8, 36, 44) for deflecting motion of said hand drive handle (14, 40, 47, 54) into motion in said guide direction of said first linear guide (5, 28).

2. The microtome according to claim 1, further comprising a detection device (37, 38, 39) for detecting motion reversal of said sample carrier (3, 30).

3. The microtome according to claim 2, further comprising a motor (26) to feed samples, and
   an electronic control circuit (39) for controlling said motor upon detecting said motion reversal of said sample carrier (3, 30).

4. The microtome according to claim 1, wherein said hand drive (40) and a second hand drive are arranged at two opposite sides of said microtome.

5. The microtome according to claim 1, wherein said deflecting device (8) comprises a plate having a circular segment shape.

6. The microtome according to claim 1, wherein said deflecting device (36) comprises a belt drive guided by a plurality of deflecting rollers (32–35, 42, 43).

7. The microtome according to claim 6, wherein said sample carrier includes a guiding slide (29, 41) and said belt drive includes a driving belt (36, 44) said sample carrier including said guiding slide having a mass, further comprising a balance weight (48) on said driving belt (36, 44) at a position where said balance weight (48) moves relative to said guiding slide (29, 41) with a reduction ratio, said balance weight (48) having a mass corresponding to the mathematical product of the mass of said sample carrier (30) including said guiding slide (29, 41) and said reduction ratio.

8. The microtome according to claim 2, wherein said deflecting device comprises a hydraulic system (51, 53, 55, 57).

9. The microtome according to claim 3, further comprising a knife carrier (2, 22) movable along a linear guideway (21) perpendicularly to said guide direction of said sample carrier slide (3, 29, 41, 50) for feeding a sample.

10. The microtome according to claim 7, wherein said path of motion of said hand drive (14, 40 47, 54) is horizontally oriented.

11. A microtome, comprising:
    a first linear guide (5, 28),
    a sample carrier slide (3,29, 41, 50) moveable in a guide direction along said first linear guide (5, 28),
    a hand drive, said hand drive including a hand drive handle (14, 40, 47, 54) moveable along a substantially linear path of motion substantially perpendicular to said guide direction of said first linear guide (5, 28), said substantially linear path of motion of said hand drive handle (14, 40, 47, 54) having a fixed direction, a deflecting device (8, 36, 44) for deflecting motion of said hand drive handle (14, 40, 47, 54) into motion in said guide direction of said first linear guide (5, 28), and a knife carrier in a front region of said microtome, said knife carrier having a back face downwardly and forwardly inclined.

12. The microtome according to claim 2, in which said deflecting device comprises a lever arm.

13. A microtome according to claim 11, further comprising a detection device (37, 38, 39) for detecting motion reversal of said sample carrier (3, 30).

14. The microtome according to claim 11, further comprising a motor (26) to feed samples, and an electronic circuit (39) for controlling said motor upon detecting said motion reversal of said sample carrier (3, 30).

15. The microtome according to claim 11, wherein said hand drive (40) and a second hand drive are arranged at two opposite sides of said microtome.

16. The microtome according to claim 11, wherein said deflecting device (8) comprises a plate having a circular segment shape.

17. The microtome according to claim 11, wherein said deflecting device comprises a lever arm.

18. The microtome according to claim 11, wherein said deflecting device (36) comprises a belt drive guided by a plurality of deflecting rollers (32–35, 42, 43).

19. The microtome according to claim 18, wherein said sample carrier includes a guiding slide (29, 41) and said belt drive includes a driving belt (36, 44), said sample carrier including said guiding slide (29, 41) having a mass, further comprising a balance weight (48) on said driving belt (36, 44) at a position, where said balance weight (48) moves relative to said guiding slide (29, 41) with a reduction ratio, said balance weight (48) having a mass corresponding to the mathematical product of the mass of said sample carrier including said guiding slide and said reduction ratio.

20. The microtome according to claim 11, wherein said deflecting device comprises a hydraulic system (51, 53, 55, 57).

21. The microtome according to claim 11, further comprising a knife carrier (2, 22) moveable along a linear guideway (21) perpendicularly to said guide direction of said carrier slide (3, 29, 41, 50) for feeding a sample.

22. The microtome according to claim 11, wherein said path of motion of said hand drive (14, 40, 47, 54) is horizontally oriented.

23. A microtome, comprising:

a first linear guide (5, 28), a sample carrier slide (3, 29, 41, 50) moveable in a guide direction along said first linear guide (5, 28), a hand drive, said hand drive including a hand drive handle (14, 40, 47, 54) moveable along a substantially linear path of motion substantially perpendicular to said guide direction of said first linear guide (5, 28), said substantially linear path of motion of said hand drive handle (14, 40, 47, 54) having a fixed direction, and a lever arm connecting said hand drive and said sample carrier and deflecting a motion of said hand drive handle into a motion in said guide direction of said first linear guide.

24. A microtome, comprising:

a first linear guide (5, 28), a sample carrier slide (3, 29, 41, 50) moveable in a guide direction along said first linear guide (5, 28), a hand drive, said hand drive including a hand drive handle (14, 40, 47, 54) moveable along a substantially linear path of motion substantially perpendicular to said guide direction of said first linear guide (5, 28), said substantially linear path of motion of said hand drive handle (14, 40, 47, 54) having a fixed direction, a lever arm connecting said hand drive and said sample carrier and deflecting a motion of said hand drive handle into a motion in said guide direction of said first linear guide, and a knife carrier in a front region of said microtome, said knife carrier having a back face downwardly and forwardly inclined.

* * * * *